United States Patent
Satake et al.

(10) Patent No.: US 9,795,291 B2
(45) Date of Patent: Oct. 24, 2017

(54) OPTICAL COHERENCE TOMOGRAPHY DEVICE AND OPTICAL COHERENCE TOMOGRAPHY CONTROL PROGRAM

(71) Applicant: NIDEK CO., LTD., Gamagori, Aichi (JP)

(72) Inventors: Norimasa Satake, Nukata (JP); Yukihiro Higuchi, Toyota (JP); Naoki Takeno, Gamagori (JP)

(73) Assignee: NIDEK CO., LTD., Gamagori (JP)

(*) Notice: Subject to any disclaimer, the term of this patent is extended or adjusted under 35 U.S.C. 154(b) by 0 days.

(21) Appl. No.: 15/184,211

(22) Filed: Jun. 16, 2016

(65) Prior Publication Data
US 2016/0367133 A1  Dec. 22, 2016

(30) Foreign Application Priority Data
Jun. 17, 2015 (JP) .................. 2015-121590

(51) Int. Cl.
*A61B 3/12* (2006.01)
*A61B 3/10* (2006.01)
*A61B 3/113* (2006.01)

(52) U.S. Cl.
CPC ............ *A61B 3/102* (2013.01); *A61B 3/1225* (2013.01); *A61B 3/113* (2013.01)

(58) Field of Classification Search
CPC .............. A61B 3/12; A61B 3/102; A61B 3/14
USPC ................... 351/206, 205, 246, 221
See application file for complete search history.

(56) References Cited

U.S. PATENT DOCUMENTS

| 2012/0120408 A1 | 5/2012 | Yasuno et al. |
| 2012/0249956 A1 | 10/2012 | Narasimha-Iyer et al. |
| 2013/0176532 A1* | 7/2013 | Sharma .................. A61B 3/102 351/206 |
| 2015/0062532 A1 | 3/2015 | Sharma et al. |

FOREIGN PATENT DOCUMENTS

WO    2010/143601 A1    12/2010

OTHER PUBLICATIONS

Nov. 16, 2016 Extended Search Report issued in European Patent Application No. 16174963.5.

* cited by examiner

*Primary Examiner* — Hung Dang
(74) *Attorney, Agent, or Firm* — Oliff PLC

(57) ABSTRACT

An optical coherence tomography device includes: an OCT optical system configured to obtain a OCT signal; a front observation optical system configured to obtain a front image of the test substance; and a controller is configured to: control the OCT optical system to obtain first temporally different OCT signals with respect to the test substance; control the front observation optical system to obtain a first front image of the test substance at the time the first OCT signals are obtained; control the front observation optical system to obtain a second front image of the test substance after that; determine whether or not the plurality of first OCT signals are good based on a positional deviation between the first and second front images; and obtain motion contrast data of the test substance when it is determined that the plurality of first OCT signals are good.

15 Claims, 5 Drawing Sheets

OPTICAL COHERENCE TOMOGRAPHY DEVICE AND OPTICAL COHERENCE TOMOGRAPHY CONTROL PROGRAM

CROSS REFERENCE TO RELATED APPLICATION

This application is based upon and claims the benefit of priority of Japanese Patent Application No. 2015-121590 filed on Jun. 17, 2015, the contents of which are incorporated herein by reference in its entirety.

BACKGROUND

The present disclosure relates to an optical coherence tomography device obtaining motion contrast data of a test substance and to an optical coherence tomography control program.

As devices for performing angiography, for example, a fundus camera and a scanning laser ophthalmoscope are known in the related art. In a case where such devices are used, a contrast agent that emits light by specific excitation light is injected into the body. By receiving light from the contrast agent, the devices obtain angiograms. That is, in the related art, the injection of the contrast agent needs to be performed.

In recent years, a device which obtains motion contrast (angiogram) by using an OCT technique without using a contrast agent has been suggested (for example, see WO2010/143601).

SUMMARY

In a case where motion contrast data is obtained using OCT, a plurality of temporally difference OCT signals which are temporally different from each other are obtained from the same site of a test substance, and the obtained plurality of OCT signals is processed, thereby obtaining motion contrast data of the test substance. However, in some cases, while the plurality of temporally different OCT signals is being obtained from the same site of the test substance, due to the motion of the test substance, the obtained plurality of OCT signals is obtained in different positions. In this case, good motion contrast data cannot be obtained.

The present disclosure is based on the problem described above, and technical objects thereof are to provide an optical coherence tomography device which can easily obtain a plurality of OCT signals of the same site with good accuracy and to provide an optical coherence tomography control program.

In order to achieve the above objects, the present disclosure includes the following constitution.

An optical coherence tomography device comprising:
an OCT optical system configured to detect a OCT signal generated based on measurement light radiated to a test substance and a reference light;
a front observation optical system configured to obtain a front image of the test substance; and
a controller is configured to:
control the OCT optical system to obtain a plurality of first OCT signals which are temporally different from each other with respect to a first region on the test substance;
control the front observation optical system to obtain a first front image of the test substance at the time the OCT optical system obtains the plurality of first OCT signals;
control the front observation optical system to obtain a second front image of the test substance after the OCT optical system obtains the plurality of first OCT signals;
detect a positional deviation between the first front image and the second front image;
determine whether or not the plurality of first OCT signals are good based on the result of the detected positional deviation; and
obtain motion contrast data of the test substance by processing the plurality of first OCT signals when it is determined that the plurality of first OCT signals are good.

A method of controlling an optical coherence tomography device including: an OCT optical system configured to obtain a OCT signal generated based on measurement light radiated to a test substance and a reference light; and a front observation optical system configured to obtain a front image of the test substance, the method comprising:
controlling the OCT optical system to obtain a plurality of first OCT signals which are temporally different from each other with respect to a first region on the test substance;
controlling the front observation optical system to obtain a first front image of the test substance at the time the OCT optical system obtains the plurality of first OCT signals;
controlling the front observation optical system to obtain a second front image of the test substance after the OCT optical system obtains the plurality of first OCT signals;
detecting a positional deviation between the first front image and the second front image;
determining whether or not the plurality of first OCT signals are good based on the result of the detected positional deviation; and
obtaining motion contrast data of the test substance by processing the plurality of first OCT signals when it is determined that the plurality of first OCT signals are good.

An optical coherence tomography device comprising:
an OCT optical system configured to obtain a OCT signal generated based on measurement light radiated to a test substance and a reference light;
a front observation optical system configured to obtain a front image of the test substance; and
a controller is configured to:
control the OCT optical system to obtain a plurality of first OCT signals which are temporally different from each other with respect to a first region on the test substance;
control the front observation optical system to obtain a first front image of the test substance and a second front image of the test substance at a different timing;
detect a positional deviation between the first front image and the second front image;
determine whether or not the plurality of first OCT signals are good based on the result of the detected positional deviation; and
obtain motion contrast data of the test substance by processing the plurality of first OCT signals when it is determined that the plurality of first OCT signals are good.

DESCRIPTION OF ILLUSTRATIVE EMBODIMENTS

Figure 1:
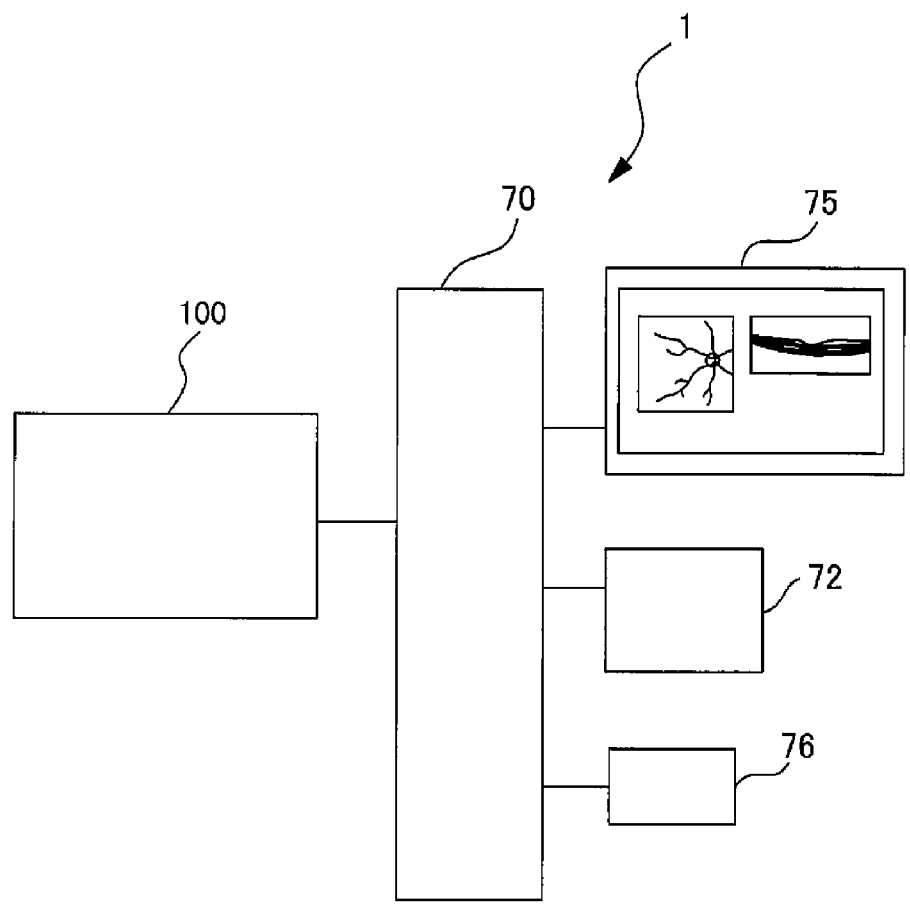
FIG. 1 is a block diagram illustrating the constitution of an optical coherence tomography device according to the present embodiment.
Figure 2:
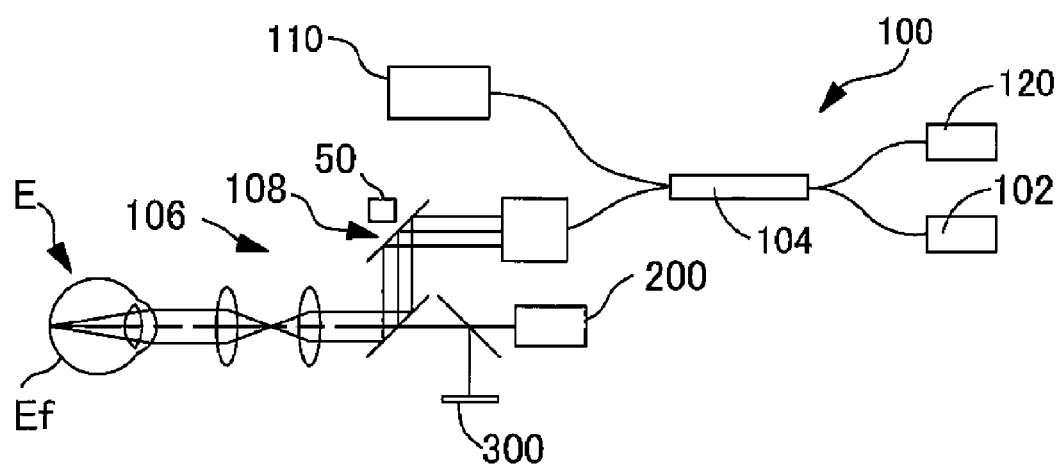
FIG. 2 is a view schematically showing an OCT optical system according to the present embodiment.

Hereinafter, one of the typical embodiments of the present invention will be described with reference to drawings. FIG. 1 is a block diagram illustrating the constitution of an optical coherence tomography device according to the present embodiment. FIG. 2 is a schematic view illustrating an OCT optical system.

An optical coherence tomography device 1 (hereinafter, described as an OCT device) processes detection signals obtained by an OCT optical system 100 (coherence optical system). According to the present embodiment, in the OCT device 1, an image captured by the OCT optical system 100 is observed on a display portion 75 (for example, a monitor). For example, the OCT device 1 is constituted with the OCT optical system, a CPU 70 (control portion), a mouse 76 (an operation portion), a memory 72 (a storage portion), and the monitor 75, and each portion is electrically connected to the CPU 70 through a bus or the like. In the following section, for example, a case where the fundus of a subject's eye is imaged as a test substance by the OCT device 1 will be described. It goes without saying that the OCT device 1 can image various biological bodies such as the ear, nose, and various organs. Furthermore, the OCT device 1 may be a device that images the anterior segment of the subject's eye, for example.

The control portion 70 controls the operation of each portion based on an arithmetic program, various control programs, and the like stored in the memory 72 (the details will be described later). As the control portion 70, the operation portion 76, the memory 72, and the monitor 75, an arithmetic processing portion, an input portion, a storage portion, and a display portion included in a commercially available personal computer (PC) may be used, and various programs may be installed on the commercially available PC.

In the present embodiment, as the OCT device 1, a device in which the OCT optical system 100 and each portion are integrated is described for example, but the present invention is not limited thereto. For instance, the OCT device 1 may do not include the OCT optical system 100. In this case, the OCT device is connected to an OCT optical system or the like which is separately provided, receives OCT signals or OCT image data, and performs various arithmetic processing based on the received information.

For example, in the present embodiment, the OCT optical system 100 includes a front observation optical system 200. It goes without saying that the OCT optical system may be integrated with the front observation optical system 200. The OCT optical system 100 irradiates fundus Ef with measurement light. The OCT optical system 100 detects the state of coherence between the measurement light reflected from the fundus Ef and reference light by using a light receiving element (a detector 120). In order to change the imaging position on the fundus Ef, the OCT optical system 100 includes an irradiation position changing unit (for example, an optical scanner 108 and a fixation target projection unit 300) changing the irradiation position of the measurement light on the fundus Ef. The control portion 70 controls the operation of the irradiation position changing unit based on the preset imaging position information and obtains a tomogram based on the light receiving signal from the detector 120.

<OCT Optical System>

The OCT optical system 100 will be described. The OCT optical system 100 has a device constitution of a so-called optical coherence tomography (OCT) and captures a tomogram of a subject's eye E. By using a coupler 104 (light splitter), the OCT optical system 100 splits light emitted from a measurement light source 102 into measurement light (sample light) and reference light. By using a measurement optical system 106, the OCT optical system 100 guides the measurement light to the fundus Ef of the eye E and the reference light to a reference optical system 110. Then, the OCT optical system 100 causes the detector 120 to receive coherent light synthesized from the measurement light reflected from the fundus Ef and the reference light.

The detector 120 detects a coherence signal generated by the measurement light and the reference light. In a case of Fourier domain OCT, the spectral intensity (spectral coherence signal) of the coherent light is detected by the detector 120, and a complex OCT signal is obtained by Fourier transform performed on the spectral intensity data.

For example, in the Fourier domain OCT, by calculating an absolute value of amplitude in the complex OCT signal obtained by performing Fourier transform on the spectral intensity data, a depth profile (A-scan signal) in a predetermined range is obtained. By lining up depth profiles in each scanning position of the measurement light used for scanning by the optical scanner 108, OCT image data (tomographic data) is obtained. Furthermore, three-dimensional OCT image data (three-dimensional tomographic data) may be obtained by performing two-dimensional scanning by using the measurement light. In addition, from the three-dimensional OCT image data, OCT front images (for example, an integrated image obtained by integrating data in the depth direction, a value of integration of spectral data in each of the positions in X- and Y-axes, luminance data in each of the positions defined by X- and Y-axes in a certain depth direction, and an image of a superficial layer of retina) may be obtained.

Based on at least two or more temporally different OCT signals which are obtained temporally different from each other with respect to the same position (same site) on the test substance, motion contrast data is obtained. That is, by performing analysis processing on at least two or more complex OCT signals, motion contrast data is obtained. For example, from the complex OCT signals, functional OCT signals are obtained. By lining up the functional OCT signals in each scanning position of the measurement light used for scanning by the optical scanner 108, functional OCT image data is obtained. In addition, by performing two-dimensional scanning in the X- and Y-axis directions by using the measurement light, three-dimensional functional OCT image data (three-dimensional motion contrast data) is obtained. Furthermore, from the three-dimensional functional OCT image data, OCT functional front images (for example, a Doppler front image and a speckle variance front image of signal and image data) are obtained. Herein, each image data may be an image data or a signal data. The motion contrast data will be specifically described later.

Examples of the Fourier domain OCT include spectral-domain OCT (SD-OCT) and swept-source OCT (SS-OCT). Furthermore, the Fourier domain OCT be time-domain OCT (TD-OCT), for example. In the case of SD-OCT, a low-coherent light source (broadband light source) is used as the light source 102, and the detector 120 is provided with a spectral optical system (spectrometer) that splits coherent light into the respective frequency components (respective wavelength components). The spectrometer consists of, for example, a diffraction grating and a line sensor. In the case of SS-OCT, as the light source 102, it is possible to use a wavelength scanning-type light source (wavelength tunable light source) which temporally changes an emission wavelength at a high speed, and a single light receiving element is provided as the detector 120, for example. The light source 102 is constituted with, for example, a light source, a fiber ring resonator, and a wavelength-selective filter. Examples of the wavelength-selective filter include a combination of a diffraction grating and a polygon mirror and a filter using Fabry.Perot etalon.

By the coupler 104, the light emitted from the light source 102 is split into a measurement light beam and a reference light beam. The measurement light beam passes through optical fiber and then is emitted to the air. Through other optical members such as the optical scanner 108 and the measurement optical system 106, the light beam is condensed on the fundus Ef. Then the light reflected from the fundus Ef returns to the optical fiber through the same optical path.

The optical scanner 108 two-dimensionally scans (X- and Y-axis directions) the fundus by using the measurement light. The optical scanner 108 is disposed in a position approximately conjugate to pupil. The optical scanner 108 consists of, for example, two galvano mirrors whose reflection angle is arbitrarily adjusted by a driving mechanism 50.

In the manner described above, the reflection (progress) direction of the light beam emitted from the light source 102 is changed, and the light beam scans any position on the fundus. As a result, the imaging position on the fundus Ef is changed. The optical scanner 108 should be constituted such that it deflects light. For example, in addition to a reflecting mirror (a galvano mirror, a polygon mirror, or a resonant scanner), an acousto-optical modulator (AOM) changing the progress (deflection) direction of light, and the like are used.

The reference optical system 110 generates reference light which is synthesized with the reflected light obtained by the reflection of the measurement light from the fundus Ef. The reference optical system 110 may be a Michelson type or a Mach-zehnder type. The reference optical system 110 is formed of, for example, a reflection optical system (for example, a reference mirror). By being reflected from the reflection optical system, the light from the coupler 104 returns to the coupler 104 and is guided again to the detector 120. For another example, the reference optical system 110 is formed of a transmission optical system (for example, optical fiber), and guides the light from the coupler 104 to the detector 120 by transmitting it without causing the light to return to the coupler 104.

The reference optical system 110 has a constituent that changes a difference in an optical path length between the measurement light and the reference light by moving optical members in the path of the reference light. For example, a reference mirror is moved in the optical axis direction. The constituent for changing the difference in the optical path length may be disposed in the path of the measurement light of the measurement optical system 106.

<Front Observation Optical System>

The front observation optical system 200 obtains front image data of a subject's eye. The front image data may be image data or signal data. For example, the front observation optical system 200 is provided to obtain front images of the fundus Ef. The front observation optical system 200 includes, for example, an optical scanner that two-dimensionally scans the fundus by using the measurement light (for example, infrared light) emitted from the light source, and a second light receiving element that receives the light reflected from the fundus through a confocal aperture disposed in a position approximately conjugate to the fundus. The front observation optical system 200 has a device constitution of a so-called scanning laser ophthalmoscope (SLO).

The front observation optical system 200 may have the constitution of a so-called fundus camera. Furthermore, for example, the front observation optical system 200 may be an infrared imaging optical system that images a test substance by using infrared light. In addition, the OCT optical system 100 may also serve as the front observation optical system 200. That is, the front image data (hereinafter, described as a front image) may be obtained using data forming a two-dimensionally obtained tomogram (OCT front image).

The front observation optical system 200 may not have a constitution in which it is integrated with the OCT device and the like. In this case, for example, the front image data obtained by the separately provided front observation optical system 200 is received by the OCT device and the like.

<Fixation Target Projection Unit>

The fixation target projection unit 300 has an optical system for leading the direction of a line of vision of the eye E. The fixation target projection unit 300 has a fixation target displayed to the eye E and can lead the eye E to a plurality of directions.

For Example, the fixation target projection unit 300 has a visible light source emitting visible light and two-dimensionally changes the position where the target is displayed. In this way, the direction of the line of vision is changed, and as a result, the imaging site is changed. For example, when the fixation target is displayed in the same direction as the imaging optical axis, the central portion of the fundus is set as the imaging site. Furthermore, when the fixation target is displayed above the imaging optical axis, the upper portion of the fundus is set as the imaging site. That is, according to the position of the target relative to the imaging optical axis, the imaging site is changed.

For example, as the fixation target projection unit 300, various constitutions are considered such as a constitution in which the fixation position is adjusted according to a lighting position of LEDs arranged in the form of matrix and a constitution in which light from a light source is used for scanning by an optical scanner and the fixation position is adjusted by controlling the lighting of the light source. Furthermore, the fixation target projection unit 300 may be an internal fixation lamp type or an external fixation lamp type.

<Control Portion>

The control portion 70 includes a CPU (processor), a RAM, a ROM, and the like. The CPU of the control portion 70 controls the entire device including the members of each of the constituents 100 to 300. The RAM temporarily stores various pieces of information. The ROM of the control portion 70 stores various programs for controlling the operation of the entire device, initial values, and the like. The control portion 70 may be constituted with a plurality of control portions (that is, a plurality of processors).

The control portion 70 is electrically connected to a nonvolatile memory 72 (storage portion), an operation portion 76 (control portion), a display portion 75 (monitor), and the like. The nonvolatile memory 72 (memory) is a non-transient storage medium which can retain the stored contents even when power supply is shut off. For example, as the nonvolatile memory 72, it is possible to use a hard disk drive, a flash ROM, a USB memory detachably mounted on the OCT device 1 and the OCT optical system 100, and the like. The memory 72 stores an imaging control program for controlling capturing of a front image and a tomogram performed by the OCT optical system 100. The memory 72 also stores a fundus analysis program which makes it possible to use the OCT device 1. In addition, the memory 72 stores various pieces of information on imaging, such as tomogram data (OCT image data) in a scan line, a three-dimensional tomogram data (three-dimensional OCT image data), a front image data (front fundus image data), and the information on the imaging position of the tomographic data. The examiner inputs various operation instructions into the operation portion 76.

The operation portion 76 outputs signals to the control portion 70 in response to the input operation instructions. As the operation portion 74, for example, at least any of a mouse, a joystick, a keyboard, and a touch panel may be used.

The monitor 75 may be either a display mounted on the body of the device or a display connected to the body. A display of a personal computer (hereinafter, referred to as "PC") may also be used, and a plurality of displays may be concurrently used. Furthermore, the monitor 75 may be a touch panel. In a case where the monitor 75 is a touch panel, the monitor 75 functions as an operation portion. On the monitor 75, various images including the tomographic data and front image data captured by the OCT optical system 100 are displayed.

<Signal Processing Method>

In the present embodiment, in which the calculation processing method for obtaining motion contrast data from OCT signals of the present embodiment is described, in order to obtain motion contrast data, the control portion 70 obtains at least two frames of temporally different coherence signals (OCT signals) in the same position.

In the present embodiment, by performing processing relating to a Doppler phase difference method and processing relating to a vector difference method, the control portion 70 obtains motion contrast data (for example, functional OCT image data) from a plurality of OCT signals. As the method for processing a plurality of OCT signals, it is possible to consider a method of calculating a phase difference of a plurality of OCT signals, a method of calculating a vector difference of a plurality of OCT signals, a method of multiplying a phase difference of a plurality of OCT signals by a vector difference thereof, and the like. In the present embodiment, the method of multiplying the phase difference by the vector difference will be described, for example.

First, the control portion 70 performs Fourier transform on the OCT signals obtained by the OCT optical system 100. Through the Fourier transform, the control portion 70 obtains a plurality of OCT signals. The plurality of OCT signals includes real number components and imaginary number components.

For obtaining a blood flow signal, temporally different images obtained in the same position need to be compared to each other. Therefore, it is preferable that the control portion 70 performs image registration based on the image information. The image registration is processing of aligning a plurality of images showing the same scene. As the causes of positional deviation between the images, for example, the motion of a subject's eye (for example, micromotion of eye during fixation, micromotion during adjustment, or pulsation) in the process of imaging is considered. Herein, even if interframe registration is performed, phase shift occurs between A-scan lines in the same image in some cases. Therefore, it is preferable to perform phase correction. Herein, the processing of registration and phase correction is for facilitating the processing of the present embodiment and is not essential.

Then, the control portion 70 calculates a phase difference for the complex OCT signals obtained in the same position at least two or more different points in time. The control portion 70 eliminates random phase differences present in a region in which a signal-to-noise ratio (S/N ratio) is low.

The control portion 70 also eliminates portions having a small phase difference so as to eliminate reflection signals from a highly reflective portion such as a nerve fiber layer (NFL). In this way, it becomes easier to make a differentiation between a signal from a highly reflective portion and a signal from a blood vessel. In the present embodiment, one frame for which the phase difference is calculated is obtained. In a case where there is a plurality of frames for which the phase difference is calculated, it is more preferable for the control portion 70 to eliminate noise by performing processing of calculating a weighted mean of the signals of the frames having undergone the processing described above.

The control portion 70 then calculates a vector difference of the complex OCT signals. For example, the control portion 70 calculates a vector difference of the complex OCT signals detected by the OCT optical system. For instance, the complex OCT signals can be represented by vectors on a complex plane. By detecting two signals obtained in the same position at different times and calculating a vector difference thereof, contrast image data in the subject's eye is generated. In a case where the vector difference is made into an image, the image can be made based on phase information in addition to the magnitude of the difference, for example. In the present embodiment, one frame for which the vector difference is calculated is obtained. In a case where there is a plurality of frames for which the vector difference is calculated, it is more preferable for the control portion 70 to eliminate noise by performing processing of calculating a weighted mean of the signals of the frames having undergone the processing described above.

The control portion 70 uses the result of phase difference calculation as a filter for the result of vector difference calculation. In the description of the present embodiment, "to perform filtering by multiplication" means to perform weighting on a certain numerical value, for example. For instance, by multiplying the result of vector difference calculation by the result of phase difference calculation, the control portion 70 performs weighting. That is, a vector difference of a portion having a small phase difference is minimized, while a vector difference of a portion having a great phase difference is emphasized. In this way, the result of vector difference calculation is weighted by the result of phase difference calculation.

In the processing of the present embodiment, the control portion 70 multiplies the result of vector difference calculation by the result of phase difference calculation, for example. In this way, the control portion 70 generates a functional OCT image data weighted by the result of phase difference calculation.

Through the multiplication of the result of vector difference calculation by the result of phase difference calculation, the disadvantages of the respective measurement methods can be eliminated, and hence image data of a blood vessel portion can be goodly obtained.

By performing the aforementioned arithmetic processing for each scan line, the control portion 70 obtains a functional OCT image data for each scan line. By obtaining functional OCT image data in a plurality of positions, it is possible to obtain three-dimensional functional OCT front image data used as a simulated angiogram.

In the present embodiment, for example, a case is described where the control portion 70 multiplies the result of the vector difference calculation by the result of the phase difference calculation so as to obtain motion contrast data. However, the present invention is not limited thereto, and motion contrast data may be obtained using the result of vector difference calculation, for example. In addition, for instance, motion contrast data may be obtained using the result of phase difference calculation. Furthermore, for example, motion contrast data may be obtained using a result of amplitude difference calculation, amplitude-decorrelation, speckle variance, phase variance, and the like.

In the present embodiment, a case is described where the control portion 70 obtains motion contrast data by using two OCT signals. However, the present invention is not limited thereto, and motion contrast data may be obtained using two or more OCT signals.

<Imaging Operation>

Hereinafter, a series of imaging operations using the OCT device 1 will be described. In the following section, for example, a case where a three-dimensional functional OCT image data is obtained will be described. It goes without saying that the technique disclosed in the present invention can be used at the time of obtaining motion contrast data. For instance, the technique can be applied in a case where a functional OCT signal is obtained or in a case where a functional OCT image data is obtained.

First, an examiner instructs a test substance to stare at a fixation target of the fixation target projection unit 300. Thereafter, while watching an observation image of an anterior eye segment, which is imaged by a camera for observing an anterior eye segment not shown in the drawing, through the monitor 75, the examiner performs an alignment operation by using the operation portion 76 (for example, a joystick not shown in the drawing) such that a measurement optical axis is positioned at the center of the pupil of the subject's eye.

For example, after the alignment operation is completed, the control portion 70 controls the OCT optical system 100 so as to obtain three-dimensional OCT image data corresponding to a preset region, and controls the front observation optical system 200 so as to obtain fundus image data (front fundus image data). Then, the control portion 70 frequently obtains three-dimensional OCT image data by the OCT optical system 100 and front fundus image data by the front observation optical system 200. Herein, the three-dimensional OCT image data includes image data obtained by two-dimensionally lining up A-scan signals relative to the X- and Y-axis directions, a three-dimensional graphic image, and the like.

The examiner sets a scanning position by using the front fundus image of the front observation optical system 200. When an imaging start signal is output from the operation portion 76, the control portion 70 controls the operation of the optical scanner 108 so as to start to obtain a three-dimensional functional OCT image data by performing two-dimensional scanning using the measurement light along the X- and Y-axis directions within a scanning range corresponding to the imaging region. As the scanning pattern, for example, raster scanning, multiple line scanning, circular scanning, scanning in a bent pattern, scanning in a curved pattern, and the like can be considered.

Figure 3:
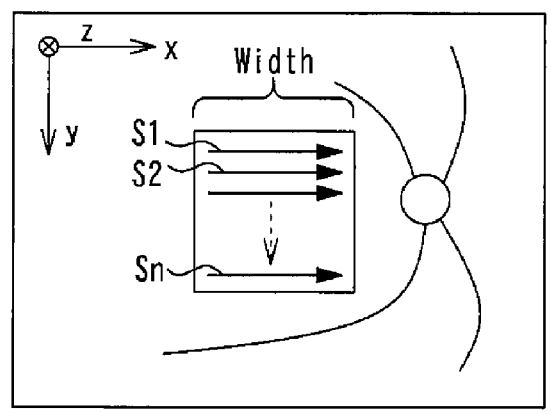
FIG. 3 is a fundus image for illustrating imaging performed in the present embodiment.

Hereinafter, the imaging operation using the OCT device 1 will be described. FIG. 3 is a schematic view for illustrating imaging of the present embodiment. In the present embodiment, for example, when an imaging start signal is output, the control portion 70 obtains a plurality of OCT signals by the OCT optical system 100 in a first scanning region on the fundus of the subject's eye. Furthermore, at the time of obtaining the plurality of OCT signals by the OCT optical system 100 in the first scanning region, the control portion 70 obtains a first front image by the front observation optical system 200. After obtaining the plurality of OCT signals by the OCT optical system 100 in the first scanning region, the control portion 70 obtains a second front image by the front observation optical system 200. Then, through image processing, the control portion 70 detects the positional deviation between the first front image and the second front image, and determines whether or not the plurality of OCT signals obtained in the first scanning region is good based on the result of the positional deviation detection. By processing the plurality of OCT signals determined as being good, the control portion 70 obtains motion contrast data of the fundus of the subject's eye.

<Obtaining OCT Signal>

Hereinafter, the operation for obtaining OCT signals will be more specifically described. For example, when an imaging start signal is output, in order to obtain three-dimensional functional OCT image data, the control portion 70 controls the driving of the optical scanner 108 such that the fundus is scanned by measurement light. For example, in response to the output of the imaging start signal, the control portion 70 controls the OCT optical system 100 so as to obtain OCT signals at a preset frame rate. Herein, the frame rate at which the OCT signals are obtained may be changed before and after the control portion 70 starts to obtain the OCT signals, or may not be changed.

The control portion 70 obtains a plurality of OCT signals in the same scanning region. Herein, the same scanning region is not necessarily completely the same scanning region, and may be approximately the same scanning region in which scanning is performed. Therefore, the control portion 70 repeats scanning in the same scanning region on the fundus. Through the scanning performed a plurality of times as above, the control portion 70 can obtain a plurality of OCT signals in the same scanning region.

For example, by using the optical scanner 108, the control portion 70 scans a plurality of times the preset first scanning region with measurement light. In the present embodiment, a case where a single scanning position (first scanning position) is set as the first scanning region will be described, for example. It goes without saying that a plurality of scanning positions (for example, two scanning positions consisting of the first and second scanning positions) may be set as a scanning region (the details will be described later).

As shown in FIG. 3, for example, by using measurement light, the control portion 70 performs scanning along the X-axis direction in the first scanning position S1 (scan line). The scanning performed in any of the X- and Y-axis directions (for example, the X-axis direction) by using measurement light as described above is called "B-scan". In the following description, a coherence signals of a single frame means an OCT signal obtained by B-scan performed once. The control portion 70 obtains the OCT signals detected by the detector 120 during scanning. In FIG. 3, the Z-axis direction is the direction of the optical axis of measurement light; the X-axis direction is a horizontal direction perpendicular to the Z-axis; and the Y-axis direction is a vertical direction perpendicular to the Z-axis.

When the first scanning ends, the control portion 70 performs the second scanning in the same position as in the first scanning. For example, the control portion 70 performs scanning along a first scan line S1 shown in FIG. 3 by using measurement light, and then performs again scanning by using measurement light. The control portion 70 obtains an OCT signal detected by the detector 120 during the second scanning. In this way, the control portion 70 can obtain temporally different OCT signals of two frames in the same scanning position. For example, in the same scanning position, the control portion 70 repeatedly obtains OCT signals, thereby obtaining OCT signals of four frames. In the present embodiment, a case where OCT signals of four frames are obtained in the same scanning position is described, for example. However, the present invention is not limited thereto, and OCT signals of at least two frames may be obtained in the same position. For instance, temporally different OCT signals of eight consecutive frames may be obtained by repeating scanning eight times in the same position, or temporally different OCT signals of two frames may be obtained by repeating scanning twice in the same position.

In a case where temporally different OCT signals can be obtained in the same position through scanning performed once, the second scanning may not be performed. For example, in a case where scanning is performed once by simultaneously using two measurement light rays whose optical axes deviate from each other by a predetermined interval, scanning does not need to be performed plural times, as long as temporally different OCT signals can be obtained in the same position in a test substance. That is, the same position is not necessarily completely the same position and may be substantially the same position in which scanning is performed. Herein, in a case where two measurement light rays are simultaneously used for scanning performed once, by the interval between the two measurement light rays, a certain blood flow velocity can be detected as a target.

<Obtaining Front Image>

Meanwhile, in response to the output of the imaging start signal, the control portion 70 controls the front observation optical system 200 so as to repeatedly obtain front images at a preset frame rate. The frame rate at which the front images are obtained may be changed before and after the control portion 70 starts to obtain the front images, or may not be changed. In the present embodiment, the frame rate at the time of obtaining OCT signals is four times higher than the frame rate at the time of obtaining front images. That is, OCT signals of four frames can be obtained within a period of time during which a front image of a single frame is obtained. In the present embodiment, the frame rate at which the OCT signals are obtained and the frame rate at which the front image is obtained should be set such that at least two OCT signals are obtained while a front image of a single frame is being obtained.

For example, in the present embodiment, the relationship between the frame rate at the time of obtaining the OCT signal and the frame rate at the time of obtaining the front image should be set such that the time taken until the end of the operation of obtaining a plurality of OCT signals in at least a single scanning region becomes equal to or shorter than the time taken until the end of the operation of obtaining a single front image. For instance, the frame rate at the time of obtaining the OCT signal and the frame rate at the time of obtaining the front image should be set such that OCT signals of frames, which are preset for obtaining motion contrast data in at least a single scanning region, can be obtained.

While obtaining a plurality of OCT signals, the control portion 70 repeats the operation of obtaining front images. By controlling each portion as described above, the control portion 70 monitors the movement (motion) of the eye while it is obtaining OCT signals. For example, through the operation of the front observation optical system 200, the control portion 70 receives light reflected from the front of the fundus. By processing the reflected light received, the control portion 70 obtains front images. Furthermore, the control portion 70 frequently stores the obtained plurality of front images in the memory 72. In this way, the control portion 70 simultaneously performs the operation of obtaining front images and the operation of obtaining OCT signals.

<Obtaining OCT Signal and Front Image Simultaneously>

Figure 4:
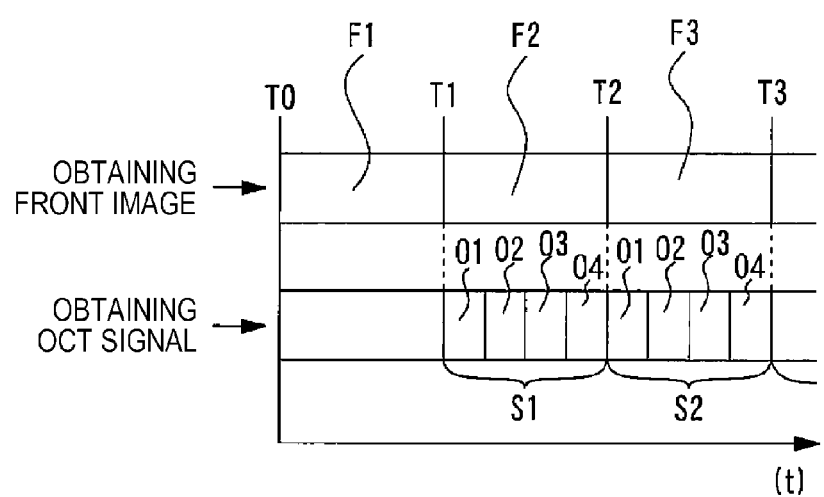
FIG. 4 is a view illustrating a relationship between an operation of obtaining OCT signals and an operation of obtaining front images.

FIG. 4 is a view illustrating the relationship between the operation of obtaining OCT signals and the operation of obtaining front images. In FIG. 4, the abscissa is a time axis (T). For example, in response to the output of an imaging start signal, the control portion 70 starts to obtain a first front image F1. When the operation of obtaining the first front image F1 ends, the control portion 70 stores the first front image F1 in the memory 72. In the present embodiment, the operation of obtaining the first front image F1 (front image of a single frame) is supposed to be completed at a point in time when a time T1 has elapsed from output timing T0 (obtainment start time) of the imaging start signal. That is, the time T1 passes until the first front image F1 is obtained.

Then, the control portion 70 starts to obtain a second front image F2. While obtaining the second front image F2, the control portion 70 also obtains a plurality of OCT signals along the first scan line S1. In the present embodiment, the frame rate at the time of obtaining the OCT signal is four times higher than the frame rate at the time of obtaining the front image. Accordingly, while a front image of a single frame is being obtained, OCT signals of four frames can be obtained. For example, during a period of time T2 (a period of time between the time T1 and time T2) when the control portion 70 obtains the second front image F2, the control portion 70 can obtain a plurality of OCT signals O1, O2, O3, and O4 in the first scan line S1. When the operation of obtaining the second front image F2 is completed, the control portion 70 stores the second front image F2 in the memory 72.

<Determining Whether or not OCT Signal is Good>

Figure 5:
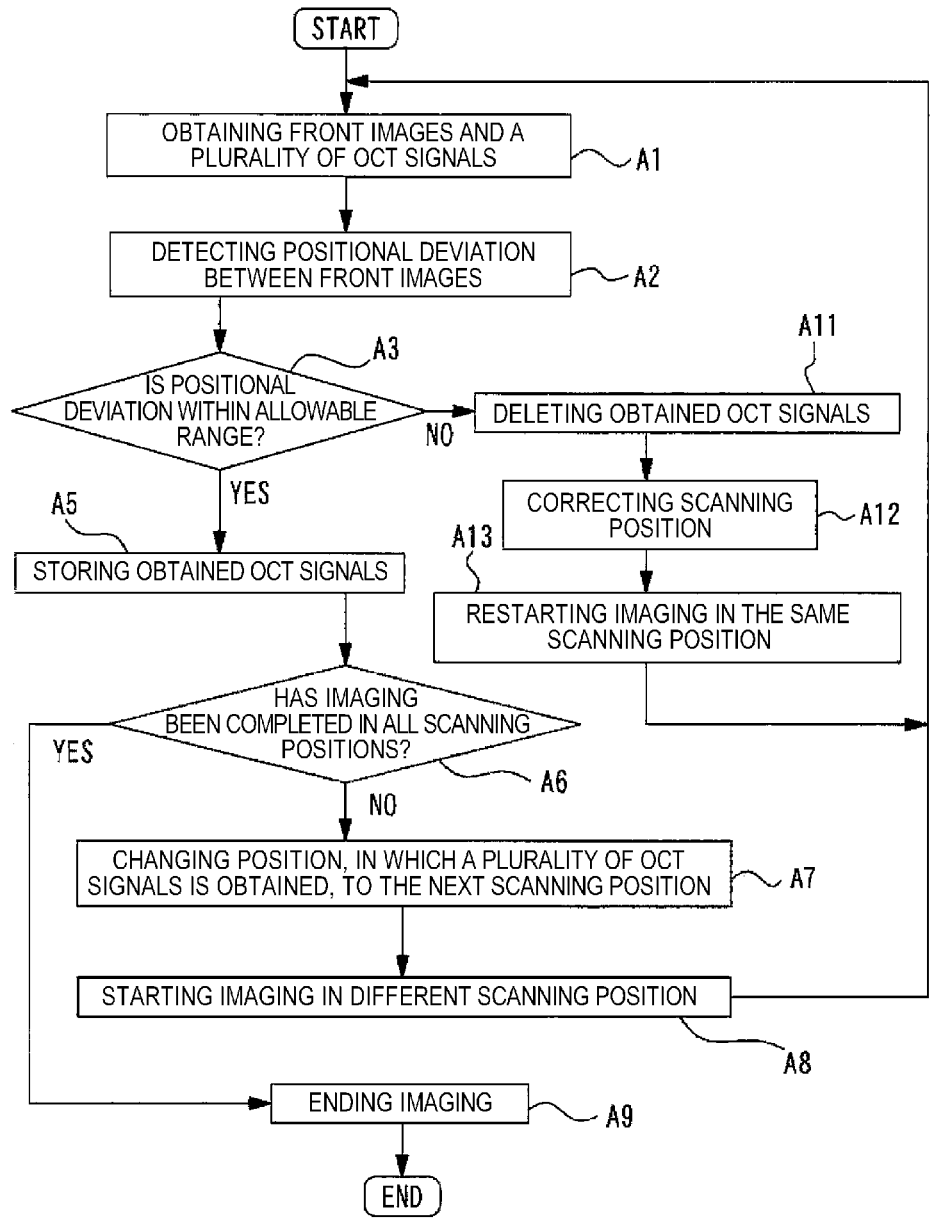
FIG. 5 shows a flowchart of determination processing.

Thereafter, the control portion 70 determines whether or not the plurality of OCT signals O1, O2, O3, and O4 obtained along the first scan line S1 is good (suitable). FIG. 5 is a flowchart showing the determination processing. In the present embodiment, whether or not the OCT signals are good is determined in real time. The determination result is used for obtaining motion contrast data by processing the plurality of OCT signals.

For example, whenever the operation of obtaining front images and a plurality of OCT signals is performed (A1), the control portion 70 performs the determination processing. For instance, the control portion 70 detects the positional deviation between the obtained front images (A2). For detecting the positional deviation, for example, the front images at the time of the operation of obtaining the plurality of OCT signals and the front images after the operation of obtaining the plurality of OCT signals are used. In the present embodiment, as the front images at the time of the operation of obtaining the plurality of OCT signals, front images obtained before the operation of obtaining the plurality of OCT signals are used. It goes without saying that the front images at the time of the operation of obtaining the plurality of OCT signals are not limited to the front images obtained before the operation of obtaining the plurality of OCT signals. For instance, as the front images at the time of the operation of obtaining the plurality of OCT signals, front images obtained while the plurality of OCT signals is being obtained may be used. In the present embodiment, as front images which are obtained after the operation of the obtaining front images at the time of the operation of obtaining the plurality of OCT signals and correspond to the front images after the operation of obtaining the plurality of OCT signals, front images obtained by the operation that is completed simultaneously with the completion of the operation of obtaining the plurality of OCT signals are used. It goes without saying that the front image after the operation of obtaining the plurality of OCT signals are not limited to the front image which is obtained by the operation that is completed simultaneously with the completion of the operation of obtaining the plurality of OCT signals. For example, as the front image after the operation of obtaining the plurality of OCT signals, front images obtained after the operation of obtaining the plurality of OCT signals (preferably, immediately obtained after the operation of obtaining OCT signals is completed) may be used.

For example, in a case where the control portion 70 determines whether or not the plurality of OCT signals O1, O2, O3, and O4 obtained in the first scan line S1 is good, the first front image F1 before the operation of obtaining the plurality of OCT signals O1, O2, O3, and O4 in the first scan line S1 and the second front image F2, which have been obtained by the operation that is completed simultaneously with the completion of the operation of obtaining the plurality of OCT signals O1, O2, O3, and O4, are used. Through image processing, the control portion 70 detects the positional deviation between the first front image F1 and the second front image F2. In this way, in the first scan line S1, the motion of the eye that is made while the plurality of OCT signals O1, O2, O3, and O4 is being obtained can be detected. That is, whether or not the positional deviation occurs at the time of the operation of obtaining the plurality of OCT signals O1, O2, O3, and O4 can be detected.

Then, for example, based on the result of the positional deviation detection, the control portion 70 determines whether or not the plurality of OCT signals O1, O2, O3, and O4 obtained in the first scan line S1 is good. For instance, the control portion 70 determines whether or not the positional deviation (deviation amount) satisfies an allowable range (for example, a predetermined threshold) (A3). For example, in a case where the deviation amount satisfies the allowable range (YES in FIG. 5), the control portion 70 determines that the plurality of OCT signals is good. Furthermore, for example, in a case where the deviation amount does not satisfy the allowable range (NO in FIG. 5), the control portion 70 determines that the plurality of OCT signals is not good.

For example, in a case where the plurality of OCT signals is determined as being good, the control portion 70 stores the plurality of OCT signals O1, O2, O3, and O4 obtained in the first scan line S1 in the memory 72 (A5). Thereafter, the control portion 70 determines whether imaging has been completed to the last scan line Sn. That is, the control portion 70 determines whether or not imaging has been completed in the entirety of scanning region (in the present embodiment, all of the scan lines) (A6). In a case where the control portion 70 determines that imaging has been completed in all of the scan lines (all of the scanning positions), the control portion 70 ends imaging (A9). Furthermore, in a case where the control portion 70 determines that imaging has not been completed in all of the scan lines, the control portion 70 continues imaging. For example, by the control portion 70, the region, in which the plurality of OCT signals O1, O2, O3, and O4 is obtained, is changed to a second scanning region (in the present embodiment, the second scan line S2) different from the first scanning region (in the present embodiment, the first scan line S1) (A7). That is, in the first scan line S1, the control portion 70 ends the operation of obtaining the plurality of OCT signals O1, O2, O3, and O4, and then stores the plurality of OCT signals O1, O2, O3, and O4 obtained in the first scan line S1 in the memory 72. Thereafter, in the second scan line S2 (second scanning position), the control portion 70 starts the operation of obtaining the plurality of OCT signals O1, O2, O3, and O4 (for examples, see FIG. 4) (A8).

For example, by controlling the optical scanner 108, the control portion 70 changes a sub-scanning position (position in the Y-axis direction), and performs scanning plural times along the second scan line S2 in a main scanning direction (X-axis direction) by using measurement light. The direction in which the scanning position is changed is not limited to the Y-axis direction, and the scanning position may be changed in the X-axis direction. In this way, wide-angle imaging can be performed in the X-axis direction. It goes without saying that the scanning position may be changed in both of the X- and Y-axis directions. As shown in FIG. 4, at the time of the operation of obtaining the plurality of OCT signals O1, O2, O3, and O4 in the second scan line S2, the control portion 70 obtains a third front image F3 in the same manner as in a case where the signals are obtained in the first scan line S1. Then, the control portion 70 determines whether or not the plurality of OCT signals O1, O2, O3, and O4 obtained in the second scan line S2 is good. In this case, for determination, the second front image F2 before the operation of obtaining the plurality of OCT signals O1, O2, O3, and O4 in the second scan line S2 and the third front image F3, which is obtained by the operation that is completed (at the time T3) simultaneously with the completion of the operation of obtaining the plurality of OCT signals O1, O2, O3, and O4, are used. Through image processing, the control portion 70 detect the positional deviation between the second front image F2 and the third front image F3, and determines whether or not the plurality of OCT signals O1, O2, O3, and O4 obtained in the second scan line S2 is good based on the result of the positional deviation detection.

In the present embodiment, a case where consecutively obtained front images (for example, the first front image F1 and the second front image F2) are used for the determination processing of determining whether or not the plurality of OCT signals is good is described, for example. However, the present invention is not limited thereto. As the front images for performing the determination processing on the OCT signals, front images before the operation of obtaining the plurality of OCT signals in the scan line and front images, which correspond to front images obtained after front images before the operation of obtaining the plurality of OCT signals and are obtained after the operation of obtaining the plurality of OCT signals, may be used. For example, an initial front image obtained as soon as imaging is started is set as a standard image. Then, in each of the scanning positions, based on the positional deviation between a front image, which is obtained as soon as the plurality of OCT signals is obtained, and the standard image, the determination processing may be performed. More specifically, for example, in a case where the determination is performed on the plurality of OCT signals O1, O2, O3, and O4 obtained in the second scan line S2, the first front image F1 and the third front image F3 may be used.

Similarly to the operation after the determination performed in the first scan line S1, in a case where the control portion 70 determines that the plurality of OCT signals is good, the region in which the plurality of OCT signals O1, O2, O3, and O4 is obtained is changed to the next scanning position (scan line). In the same manner as described above, the control portion 70 performs the determination processing while obtaining OCT signals and front images, and performs scanning plural times by using measurement light in each of the scan lines to the last scan line Sn, thereby obtaining the plurality of OCT signals in each of the scan lines. That is, as shown in FIG. 3, the control portion 70 performs raster scanning (scanning performed in positions on a horizontal line) by using measurement light, and obtains temporally different OCT signals of at least two or more frames (in the present embodiment, four frames) in each of the scan lines (S1 to Sn). In this way, it is possible to obtain three-dimensional information on the fundus. Herein, even in a case where imaging has not been completed to the last scanning position, if an imaging stop operation is performed by the examiner, the imaging operation may be ended at that point in time. In this way, by determining whether or not the obtained plurality of OCT signals is good and changing the scanning region based on the determination result, the plurality of OCT signals in each of the scanning regions can be more rapidly obtained.

In contrast, for example, in a case where the control portion 70 determines that the plurality of OCT signals is not good, the control portion 70 reobtains the plurality of OCT signals in the first scan line S1. For instance, the control portion 70 deletes the plurality of OCT signals O1, O2, O3, and O4 and the first front image F1 obtained in the first scan line S1 (A11) and starts to reobtain the signals. Based on the deviation amount between the first front image F1 and the second front image F2, the control portion 70 controls the optical scanner 108 and corrects the scanning position (A12). For example, the control portion 70 appropriately controls the driving of two galvano mirrors of the optical scanner 108 such that the scanning position deviation is corrected. After the correction of the scanning position, the control portion 70 restarts the operation of obtaining the plurality of OCT signals in the first scan line S1 (A13).

Before obtaining the plurality of OCT signals, the control portion 70 obtains a front image after the correction of the scanning position. That is, for example, the control portion 70 obtains a front image at the time of the operation of reobtaining plurality of OCT signals. After reobtaining the plurality of OCT signals, based on the positional deviation between the front image at the time of the operation of reobtaining the plurality of OCT signals and a front image which is obtained by the operation that is completed simultaneously with the completion of the operation of reobtaining the plurality of OCT signals, the control portion 70 determines whether or not the reobtained plurality of OCT signals is good. Then, based on the determination result, the control portion 70 determines whether it will move on to scanning of the next scanning position or perform again scanning in the same scanning position. In a case where the control portion 70 fails plural times to goodly obtain OCT signals, the control portion 70 may end imaging by displaying an error message or the like (for example, a message for inducing the examiner to reset the imaging position or to readjust the imaging conditions). In this way, in a case where the control portion 70 fails to goodly obtain the plurality of OCT signals, by reobtaining the plurality of OCT signals, the plurality of OCT signals in each of the scanning regions can be accurately obtained.

<Obtaining Motion Contrast Data>

By processing the plurality of OCT signals determined as being good, the control portion 70 obtains motion contrast data (in the present embodiment, three-dimensional functional OCT image data is obtained) on the fundus of the subject's eye. For example, in a case where the control portion 70 moves on to the operation of obtaining the plurality of OCT signals in the next scan line, the control portion 70 performs arithmetic processing on the plurality of OCT signals that has already been obtained in each of the scan lines.

For example, after obtaining the plurality of OCT signals in the first scan line S1, the control portion 70 moves the scanning position (obtainment position) of the plurality of OCT signals to the second scan line S2 from the first scan line S1. When the operation of obtaining the plurality of OCT signals is started in the second scan line S2, the control portion 70 starts to perform arithmetic processing on the obtained plurality of OCT signals in the first scan line S1. That is, while the OCT signals are being obtained in the second scan line S2, the control portion 70 starts to perform arithmetic processing on the plurality of OCT signals corresponding to the first scan line S1 and obtains functional OCT image data in the first scan line S1. While obtaining the plurality of OCT signals in each of the scan lines by performing the aforementioned processing for each of the scan lines, the control portion 70 continuously obtains functional OCT image data for each scan line. Then, by obtaining the functional OCT image data in the plurality of positions (scan lines) described above, it is possible to obtain three-dimensional functional OCT front image data which is a simulated angiogram (image which can be used as an angiogram). In this way, by performing arithmetic processing for obtaining motion contrast data during the operation of obtaining the plurality of OCT signals, motion contrast data can be more rapidly obtained. In the present embodiment, in a case where the control portion 70 moves on to the operation of obtaining the plurality of OCT signals in the next scan line, the control portion 70 performs arithmetic processing on the plurality of OCT signals that has already been obtained in each of the scan lines. However, the present invention is not limited to thereto. For example, the control portion 70 may obtain the plurality of OCT signals in each of the scan lines and then start the arithmetic processing on the plurality of OCT signals in each of the scan lines.

As described above, based on the detection result of the positional deviation between the front image at the time of the operation of obtaining the plurality of OCT signals and the front image after the operation of obtaining the plurality of OCT signals in a predetermined scanning region, whether or not the plurality of OCT signals obtained in the predetermined scanning region is good is determined, and in this way, it is possible to collectively determine whether or not the plurality of OCT signals obtained in the same site (same scanning region) is good. Therefore, it is easy to check whether or not the obtained plurality of OCT signals has been goodly imaged. As a result, it is possible to easily obtain the plurality of OCT signals in the same scanning region with high accuracy.

<Modification Example>

In the present embodiment, after the operation of obtaining the first front image F1 is completed, the operation of obtaining the plurality of OCT signals in the first scan line S1 is started. However, the present invention is not limited thereto, and in response to the output of an imaging start signal, the operation of obtaining the first front image F1 and the operation of obtaining the plurality of OCT signals may be started simultaneously. In this case, for determining whether or not the plurality of OCT signal is good, the plurality of OCT signals simultaneously obtained at the time of the operation of obtaining the first front image F1 (the plurality of OCT signals obtained as soon as imaging is started) is deleted, and by using the plurality of OCT signals simultaneously obtained at the time of the operation of obtaining the second front image F2, the determination processing for a plurality of OCT signals is started. For example, in the first scan line S1, OCT signals of eight frames (OCT signals of four frames at the time of the operation of obtaining the first front image F1 and OCT signals of four frames at the time of the operation of obtaining the second front image F2) are obtained, and the OCT signals of four frames at the time of the operation of obtaining the first front image F1 are deleted.

Figure 6:
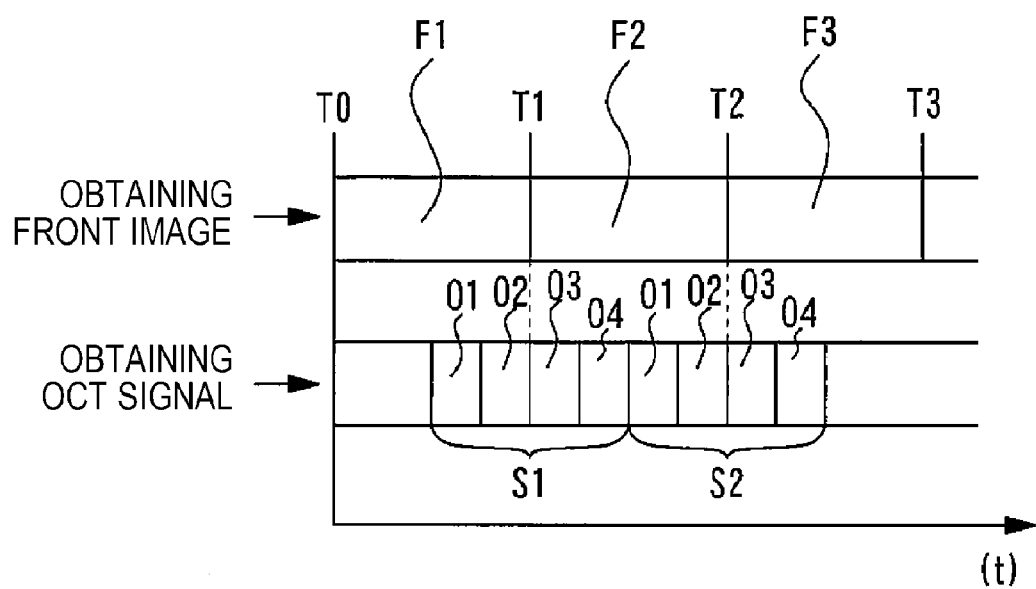
FIG. 6 is a view illustrating a modification example of a relationship between the operation of obtaining OCT signals and the operation of obtaining front images.

In the present embodiment, a case where the timing of starting the operation of obtaining front images is in synchronization with and the time of starting the operation of obtaining the plurality of OCT signals in a predetermined scanning region is described, for example. However, the present invention is not limited thereto, and the timing of starting the operation of obtaining the plurality of OCT signals in a predetermined scanning region may not be in synchronization with the timing of starting the operation of obtaining front images. For instance, as shown in FIG. 6, while the operation of obtaining the first front image F1 is being performed (for example, after the elapse of half of the time T1), the operation of obtaining the plurality of OCT signals in the first scan line S1 is started. In this case, at the time of the operation of obtaining the plurality of OCT signals O1, O2, O3, and O4 in the first scan line S1, the first front image F1 and the second front image F2 are obtained. That is, the determination processing for the plurality of OCT signals O1, O2, O3, and O4 in the first scan line S1 is performed using the positional deviation between the first front image F1 and the second front image F2. Furthermore, the operation of obtaining the plurality of OCT signals O1, O2, O3, and O4 in the second scan line S2 is started while the operation of obtaining the second front image F2 is being performed (for example, after the elapse of half of the time T2). Based on the second front image F2 and the third front image F3, determination processing is performed on the plurality of OCT signals O1, O2, O3, and O4 in the second scan line S2.

In the present embodiment, based on the detection result of the positional deviation between the front image of a single frame at the time of the operation of obtaining the plurality of OCT signals in a predetermined scanning region and the front image of a single frame after the operation of obtaining the plurality of OCT signals, whether or not the plurality of OCT signals obtained in the predetermined scanning region is good is determined. However, the present invention is not limited thereto. For example, in a case where a front observation optical system (for instance, an infrared observation optical system) is used which can obtain a plurality of front images while obtaining the plurality of OCT signals, the determination processing may be performed by selecting a single front image (for example, the latest front image) from the plurality of front images. Furthermore, the determination processing may be performed on the plurality of OCT signals by using all of the plurality of front images, for example.

In the present embodiment, a case where a single scanning position (first scanning position) is set as the first scanning region is described, for example. However, the present invention is not limited thereto, and a plurality of scanning positions may be set as the scanning region. For instance, two scanning positions consisting of the first scanning position and the second scanning position may be set as the first scanning region scanned by measurement light. In this case, for example, if a frame rate at which front images and OCT signals are obtained is the frame rate exemplified in the present embodiment (if a frame rate at which OCT signals are obtained is four times higher than a frame rate at which front images are obtained), while a front image of a single frame is being obtained, OCT signals of two frames are obtained in the first scanning position, and OCT signals of two frames are obtained in the second scanning position. That is, in a case where determination is performed based on the detection result of the positional deviation between the front image of a single frame at the time of the operation of obtaining the plurality of OCT signals in a predetermined scanning region (for example, the first scanning region) and the front image of a single frame after the operation of obtaining the plurality of OCT signals, whether or not the plurality of OCT signals in the two scanning positions is good can be collectively determined. Furthermore, by processing each of the plurality of OCT signals obtained in at least two or more scanning positions (in the present embodiment, two scanning positions), the control portion 70 obtains motion contrast data of each of the scanning positions on the fundus of the subject's eye. In this way, while the operation of detecting the positional deviation between front images, which are obtained at the time of the operation of obtaining the plurality of OCT signals and after the operation of obtaining the plurality of OCT signals, is being performed once, motion contrast data of a plurality of scanning positions can be obtained. As a result, imaging can be more rapidly completed.

In a case where a plurality of scanning positions is set as the scanning region, the operation of obtaining the plurality of OCT signals in each of the scanning positions can be performed in any order. For example, in a case where two scanning positions consisting of the first scanning position and the second scanning position are set as the first scanning region scanned by measurement light, after an OCT signal of a single frame is obtained in the first scanning position, and an OCT signal of a single frame is obtained in the second scanning position. Then, an OCT signal of a single frame is obtained in the first scanning position, and then an OCT signal of a single frame is obtained in the second scanning position. That is, by alternately obtaining OCT signals in the first and second scanning positions, OCT signals of two frames can be obtained in each of the scanning positions. In addition, for example, in a case where an OCT signal of a single frame is obtained in the first and second scanning positions, the OCT signal in the first scanning position and the OCT signal in the second scanning position may be simultaneously obtained while scanning is being performed once.

In the present embodiment, in a case where it is determined that the OCT signals are not good, imaging is performed again in the same scanning region. However, the present invention is not limited thereto, and the OCT signals of the scanning region, from which OCT signals determined as not being good are obtained, may be imaged again after the imaging is completed in all of the scanning positions. Furthermore, the scanning region from which OCT signals are not goodly obtained may be reported to the examiner. In this case, based on the reported information, the examiner may perform again imaging or the like.

In the present embodiment, a case where the front image of the fundus is obtained to detect the positional deviation of the fundus of the subject's eye is described, but the present invention is not limited thereto. For example, front images of the anterior segment of the subject's eye may be captured, and based on the positional deviation between the front images of the anterior segment, imaging may be performed in the fundus.

In the present embodiment, an optical coherence tomography device obtaining OCT signals is described, for example. However, the present disclosure is not limited thereto, and the technique of the present disclosure can be applied to any of devices that obtain motion contrast data from a plurality of signals (for instance, imaging signals obtained by a fundus imaging device having a wavefront compensation function).

The present invention is not limited to the device described in the present embodiment. For example, arithmetic software (program) for optical coherence tomography performing functions of the present embodiment described above is supplied to a system or a device through network or various storage media. Then, a computer (for example, CPU) of the system or the device can read out and execute the program.

DESCRIPTION OF REFERENCE NUMERALS AND SIGNS

1 optical coherence tomography device
70 control portion
72 memory
75 monitor
76 operation portion
100 coherence optical system (OCT optical system)
108 optical scanner
120 detector
200 front observation optical system
300 fixation target projection unit

What is claimed is:

1. An optical coherence tomography device comprising:
an OCT optical system configured to detect a OCT signal generated based on measurement light radiated to a test substance and a reference light;
a front observation optical system configured to obtain a front image of the test substance; and
a controller is configured to:
control the OCT optical system to obtain a plurality of first OCT signals which are temporally different from each other with respect to a first region on the test substance;
control the front observation optical system to obtain a first front image of the test substance at the time the OCT optical system obtains the plurality of first OCT signals;
control the front observation optical system to obtain a second front image of the test substance after the OCT optical system obtains the plurality of first OCT signals;
detect a positional deviation between the first front image and the second front image;
determine whether or not the plurality of first OCT signals are good based on the result of the detected positional deviation; and
obtain motion contrast data of the test substance by processing the plurality of first OCT signals when it is determined that the plurality of first OCT signals are good,
wherein a timing of starting the control of the OCT optical system to obtain the plurality of first OCT signals is not in synchronization with the timing of starting the control of the front observation optical system to obtain the first front image or to obtain the second front image.

2. The optical coherence tomography device according to claim 1, wherein when the controller determines that the plurality of first OCT signals are good, the controller controls the OCT optical system to obtain a plurality of second OCT signals with respect to a second region on the test substance, the second region being different from the first region.

3. The optical coherence tomography device according to claim 1, wherein in a case where the controller determines that the plurality of OCT signals are not good, the controller obtains the plurality of first OCT signals with respect to the first region again.

4. The optical coherence tomography device according to claim 3, wherein
the OCT optical system corrects a scanning position in the first region based on the positional deviation when the OCT optical system obtains the plurality of first optical signals with respect to the first region again.

5. The optical coherence tomography device according to claim 1,
wherein the first region includes a plurality of positions on the test substance,
the controller controls the first OCT optical system to obtain the plurality of first OCT signals with respect to each of the plurality of positions on the test substance, and
the controller obtains the motion contrast data in each of the scanning positions on the test substance by processing each of the plurality of first OCT signals obtained in the plurality of positions.

6. The optical coherence tomography device according to claim 2, wherein while the OCT optical system obtains the plurality of second OCT signals with respect to the second scanning region, the controller obtains the motion contrast data of the test substance in the first scanning region by processing the plurality of first OCT signals obtained with respect to the first scanning region.

7. The optical coherence tomography device according to claim 1, wherein
when the positional deviation exceeds a threshold, the controller determines that the plurality of first OCT signals are not good, and
when the positional deviation does not exceeds the threshold, the controller determines that the plurality of first OCT signals are good.

8. The optical coherence tomography device according to claim 1, wherein
the first region includes a plurality of positions on the test substance,
the controller controls the first OCT optical system to obtain the plurality of first OCT signals with respect to each of the plurality of positions on the test substance,
the controller collectively determines whether or not the plurality of first OCT signals with respect to the plurality of positions on the test substance are good based on the result of the detected positional deviation, and the controller obtains the motion contrast data of the test substance by processing the plurality of first OCT signals when it is collectively determined that the plurality of first OCT signals with respect to the plurality of positions on the test substance are good.

9. The optical coherence tomography device according to claim 1, wherein after the controller controls the OCT optical system to obtain the plurality of first OCT signals, the controller controls the OCT optical system to obtain a plurality of second OCT signals with respect to a second region on the test substance, the second region being different form the first region, if the controller determines that the plurality of first OCT signals are not good, the controller controls the OCT optical system to obtain the plurality of first optical signals with respect to the first region again after the controller controls the OCT optical system to obtain the plurality of second OCT signals.

10. The optical coherence tomography device according to claim 9, wherein the OCT optical system corrects a scanning position in the first region based on the positional based on the positional deviation when the OCT optical system obtains the plurality of first optical signals with respect to the first region again.

11. The optical coherence tomography device according to claim 1, wherein the controller controls the OCT optical system to obtain a plurality of the OCT signals of the scanning region from which OCT signals determined as not being good again after the controller controls the OCT optical system to obtain the plurality of OCT signals in all of the scanning positions.

12. The optical coherence tomography device according to claim 1, wherein each of the plurality of first OCT signals includes eight consecutive frames.

13. A method of controlling an optical coherence tomography device including: an OCT optical system configured to obtain a OCT signal generated based on measurement light radiated to a test substance and a reference light; and a front observation optical system configured to obtain a front image of the test substance, the method comprising:

controlling the OCT optical system to obtain a plurality of first OCT signals which are temporally different from each other with respect to a first region on the test substance;

controlling the front observation optical system to obtain a first front image of the test substance at the time the OCT optical system obtains the plurality of first OCT signals;

controlling the front observation optical system to obtain a second front image of the test substance after the OCT optical system obtains the plurality of first OCT signals;

detecting a positional deviation between the first front image and the second front image;

determining whether or not the plurality of first OCT signals are good based on the result of the detected positional deviation; and obtaining motion contrast data of the test substance by processing the plurality of first OCT signals when it is determined that the plurality of first OCT signals are good, wherein a timing of starting the control of the OCT optical system to obtain the plurality of first OCT signals is not in synchronization with the timing of starting the control of the front observation optical system to obtain the first front image or to obtain the second front image.

14. The optical coherence tomography device according to claim 13, wherein one of the first front image and the second front image is obtained at the time the plurality of first OCT signals are obtained, and the other of the first front image and the second front image is obtained at a time other than the time the plurality of first OCT signals are obtained.

15. An optical coherence tomography device comprising:

an OCT optical system configured to obtain a OCT signal generated based on measurement light radiated to a test substance and a reference light;

a front observation optical system configured to obtain a front image of the test substance; and a controller is configured to:

control the OCT optical system to obtain a plurality of first OCT signals which are temporally different from each other with respect to a first region on the test substance;

control the front observation optical system to obtain a first front image of the test substance and a second front image of the test substance at a different timing;

detect a positional deviation between the first front image and the second front image;

determine whether or not the plurality of first OCT signals are good based on the result of the detected positional deviation; and obtain motion contrast data of the test substance by processing the plurality of first OCT signals when it is determined that the plurality of first OCT signals are good, wherein a timing of starting the control of the OCT optical system to obtain the plurality of first OCT signals is not in synchronization with the timing of starting the control of the front observation optical system to obtain the first front image and the second front image.

* * * * *